(12) United States Patent
Weimer et al.

(10) Patent No.: US 7,651,582 B2
(45) Date of Patent: Jan. 26, 2010

(54) WOOD ADHESIVES CONTAINING SOLID RESIDUES OF BIOMASS FERMENTATIONS

(75) Inventors: Paul J. Weimer, Madison, WI (US); Linda F. Lorenz, Middleton, WI (US); Anthony H. Conner, Mt. Horeb, WI (US); Charles R. Frihart, Dana, WI (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/151,353

(22) Filed: May 6, 2008

(65) Prior Publication Data

US 2008/0202684 A1 Aug. 28, 2008

Related U.S. Application Data

(63) Continuation of application No. 11/453,605, filed on Jun. 15, 2006, now abandoned, which is a continuation of application No. 10/838,752, filed on May 4, 2004, now abandoned.

(60) Provisional application No. 60/468,311, filed on May 6, 2003.

(51) Int. Cl.
  *C09J 201/00* (2006.01)
  *C09J 201/02* (2006.01)
  *C08L 61/04* (2006.01)
(52) U.S. Cl. ........................ 156/336; 156/335
(58) Field of Classification Search ............... 156/336, 156/335
  See application file for complete search history.

(56) References Cited

U.S. PATENT DOCUMENTS 5,733,539 A * 3/1998 Kitano et al. ................. 424/84

* cited by examiner

*Primary Examiner*—Nathan M Nutter
(74) *Attorney, Agent, or Firm*—John Fado; Randall E. Deck; Lesley Shaw

(57) ABSTRACT

A bioadhesive composition for bonding together adjacent surfaces of wood comprises a microbially-produced fermentation residue containing adherent microbial cells and glycocalyx. This residue finds particular application as a replacement for a significant amount of phenol-formaldehyde (PF) or other conventional adhesive component commonly used in the production of plywood and other wood products.

9 Claims, 6 Drawing Sheets

WOOD ADHESIVES CONTAINING SOLID RESIDUES OF BIOMASS FERMENTATIONS

BACKGROUND OF THE INVENTION

1. Field of the Invention

This invention relates to the use of a microbially-produced fermentation residue as a component in adhesives for wood products.

2. Description of the Prior Art

Over the last several decades renewable resources have contributed an increasing share of fuel and chemical production in developed countries. One of the largest of these contributors has been ethanol produced by fermentation and used as a gasoline additive. Commercial ethanol is produced almost exclusively by saccharification of starch (usually from corn) and subsequent fermentation of the sugars by *Saccharomyces* yeast. The development of fermentations based on cellulosic biomass, instead of on starch, has remained attractive because of the low cost and great abundance of cellulosic materials, either directly from biomass energy crops, or from agroforestry wastes (Lynd et al., Biotechnol. Prog. 15:777-793, 1999).

Though research on bioconversion of cellulosic materials to ethanol has largely focused on chemical or enzymatic hydrolysis of biomass with subsequent fermentation of sugars by yeast, the process is not economically viable for a variety of reasons (Lynd et al. 1999 supra). The chemical hydrolysis route suffers from a requirement for postprocessing (e.g., neutralization of the hydrolysate, the costly handling of waste products, and the removal or treatment of fermentation inhibitors formed during hydrolysis). The enzymatic route involves high costs associated with producing fungal enzyme with low inherent specific activities. A potential alternative route for cellulose bioconversion involves processes in which enzyme production, enzymatic hydrolysis and sugar fermentation occurs in a single bioreactor (Lynd et al. 1999 supra; Lynd et al., Microbiol. Molec. Biol. Revs. 66:506-577, 2002). There is little doubt that the economic viability of biomass conversion processes will ultimately depend on the marketability of co-products produced during the bioconversion process. This is implicit in the modern notion of a biorefinery that is envisioned to ultimately produce a suite of biologically-derived commercial products (Lynd et al. 1999 supra).

The ruminal cellulolytic bacterium *Ruminococcus albus* can ferment cellulose, some hemicelluloses (e.g., xylans and glucomannans) and pectin, to produce a mixture of ethanol, acetic acid, $H_2$ and $CO_2$ (Hungate, Academic Press, New York, N.Y., 1966; Pavlostathis et al., Appl. Environ. Microbiol. 54:2655-2659, 1988). A necessary prerequisite of the *R. albus* cellulose fermentation is adherence of the bacteria to cellulose, which is mediated by a variety of adhesins that include cellulose binding domains of cellulolytic enzymes; components of polycellulosomal organelles; pilin-like proteins and exopolysaccharide-containing glycocalyx materials (Miron et al., J. Dairy Sci. 84:1294-1309, 2001; Weimer, J. Dairy Sci. 79:1496-1502, 1996). The glycocalyx is relatively resistant to disruption by physical and chemical forces normally encountered by the organism in culture or in the rumen environment.

In unrelated work, the incorporation of natural products into chemical, industrial adhesive formulations has been explored (Loetscher, U.S. Pat. No. 1,959,433, 1934, Feigley, U.S. Pat. No. 2,868,743, 1959, Conner et al., J. Wood Chem. Technol. 6:591-613, 1986, Addition to phenol-formaldehyde (PF) resins of carbohydrates with large amounts of reducing end groups is known to result in loss of adhesive properties if the carbohydrate exceeds about 10 per cent of the weight of the PF resin (Feigley 1959 supra). By contrast, adhesive properties of PF resins are maintained upon addition of up to 30-50 per cent of the total adhesive weight of sucrose, methyl monosaccharides or sugar alcohols (Conner et al. 1986 supra).

Proteins of biological origin (e.g., blood or soybeans) were commonly used in the adhesives industry prior to the development of formaldehyde-based synthetic chemical adhesives. Neither these biological materials, nor most carbohydrates, are typically involved in adhesion in nature. However they can display adhesive properties when properly denatured, mixed with other materials, and cured under heat and pressure (Lambuth, Pizzi A., Mittal K. L., (eds) Handbook of Adhesive Technology, Marcel Dekker, New York, N.Y., pp. 259-282, 1994). The resulting mixed resins show acceptable strength under dry conditions, but often display reduced adhesive strength under wet or humid conditions (Lambuth 1994).

SUMMARY OF THE INVENTION

We have now invented an adhesive composition useful for producing wood products, the adhesive composition comprising a microbially-produced fermentation residue containing adherent microbial cells and glycocalyx. This residue finds particular application as a replacement for a significant amount of phenol-formaldehyde (PF) resin commonly used in the production of plywood and other wood products.

In accordance with this invention, it is an object of the invention to provide a novel adhesive material for use in the production of wood-based products.

It is a further object of this invention to provide a bioadhesive replacement for at least a portion of the PF resin currently used in lay-up of plywood and other glued wood products.

It is also an object of the invention to provide an industrial use for solid residues resulting from fermentative conversions of cellulosic substrates.

Other objects and advantages of this invention will become readily apparent from the ensuing description.

DEPOSIT OF BIOLOGICAL MATERIAL

Figure 1A:
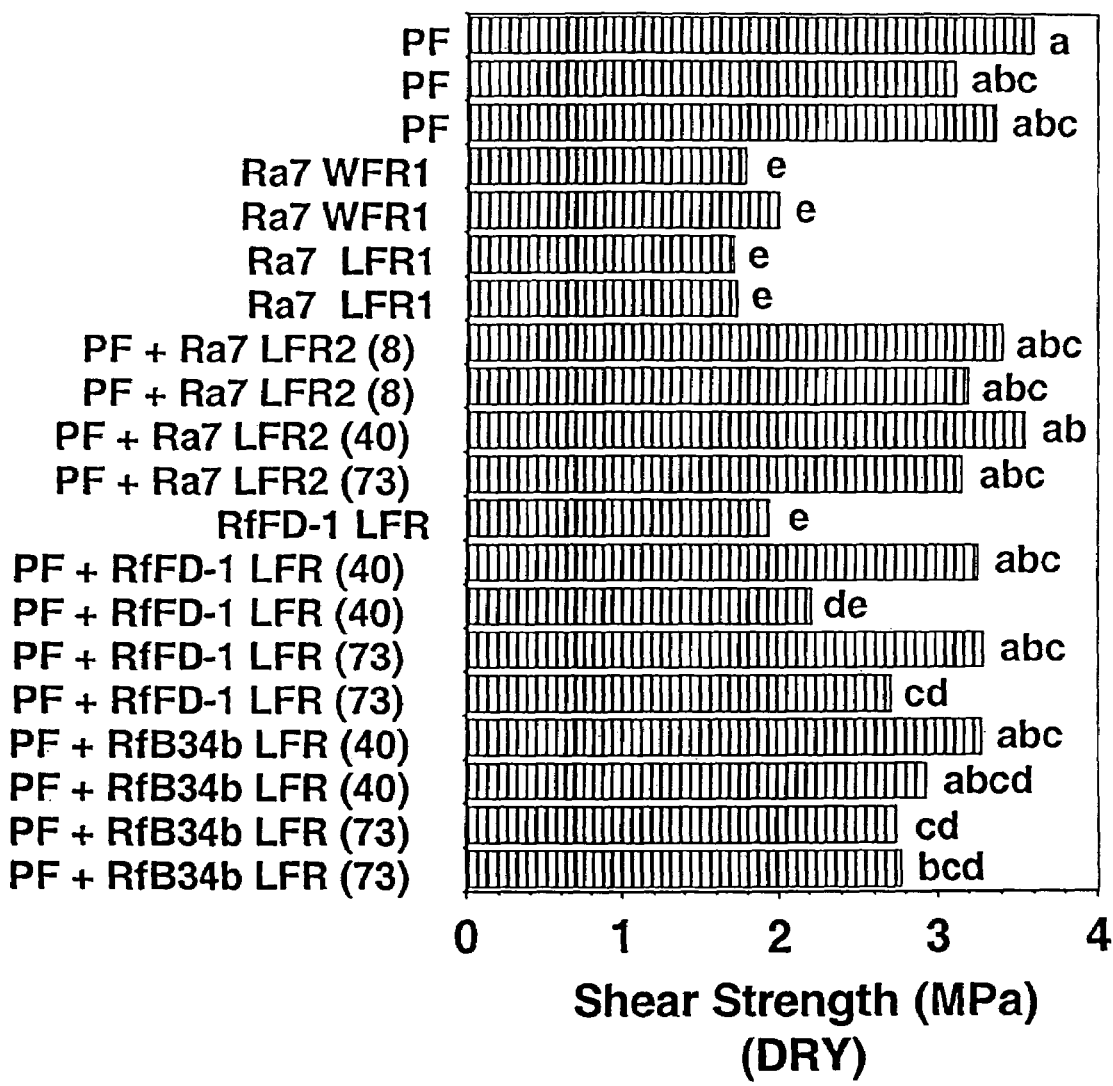
FIG. 1A is a bar graph illustrating shear strength.

*Ruminococcus albus* strain 7 and *Ruminococcus flavefaciens* strain FD-1 were deposited on May 5, 2003, under the provisions of the Budapest Treaty in the Agricultural Research Culture Collection (NRRL) in Peoria, Ill., and have been assigned Accession Nos. NRRL B-30653 and NRRL B-30654, respectively.

DETAILED DESCRIPTION

The expression "fermentation residue" as used herein refers to the solid residue resulting from the fermentation of certain microbes that produce any one, or a combination of: adhesins that include cellulose binding domains of cellulolytic enzymes; components of polycellulosomal organelles; pilin-like proteins; and exopolysaccharide-containing glycocalyx materials.

The expression "glycocalyx material" as used herein refers to any network of polysaccharide- and/or protein-containing material extending outside of the cell.

Agricultural biomass is defined herein to mean any cellulosic or lignocellulosic plant material, especially waste material, including but not limited to, leaves and stalks of both woody and non-woody plants. The term "woody" is used herein both in the botanical sense to mean "comprising wood"; that is, composed of extensive xylem tissue as found in trees and shrubs, and also in the sense of "being woodlike". Accordingly, "nonwoody" refers to materials lacking these characteristics.

Agricultural biomass from woody plants would include orchard prunnings, chaparral, mill waste (such as bark, chips, shavings, sawdust, and the like), urban wood waste (such as discarded lumber, wood pallets, crates, tree and brush trimmings, etc.), municipal waste (such as newspaper and discarded grocery produce), logging waste and forest thinnings (tree tops, limbs and cull material), short-rotation woody crops such as poplar and cottonwood, and industrial waste (such as wood pulp sludge).

The preponderance of biomass from non-woody plants is derived from monocotyledonous plants, and especially grassy species belonging to the family Gramineae. Of primary interest are gramineous agricultural residues; that is, the portion of grain-bearing plants that remain after harvesting the seed. Illustrative of such residues, without limitation thereto, are wheat straw, oat straw, rice straw, barley straw, rye straw, flax straw, sugar cane, corn stover, corn stalks, corn cobs, corn husks, and the like. Also included within this definition are grasses not conventionally cultivated for agricultural purposes, such as prairie grasses (e.g. big bluestem, little bluestem, Indian grass), gamagrass, and foxtail. Certain dicotyledonous plants, such as alfalfa (*Medicago sativa*) and other leguminous forage crops would also be useful as a source of fermentable biomass.

Other agricultural byproducts in the category of biomass include waste streams components from commercial processing of crop materials (such as sugar beet pulp, citrus fruit pulp, seed hulls, and the like), lawn clippings, seaweed, etc.

The starting material for use herein may also be an agricultural biomass hydrolysate. The term "agricultural biomass hydrolysate" or variations thereof is used herein to refer to any of the aforementioned biomass materials that have been pretreated with acid to solubilize the xylan and cellulose in the material and to release sugar monomers. The hydrolysate may have residual xylan or may have been treated to remove the xylan prior to the detoxification treatment described hereafter.

Any of the aforementioned biomass materials would be useful herein as substrates for production of the fermentation material as either a primary product or as a by-product, such as in conversion of the biomass to ethanol.

Organisms useful for producing a suitable fermentation residue from the aforementioned biomass materials in accordance with the invention include any that can be fermented under conditions that will yield a readily recoverable amount of the residue comprising an extracellular polymeric matrix for sticking to the cellulosic biomass substrate. Of particular interest is any strictly anaerobic cellulose-digesting bacterium that adheres to cellulose fibers via a thick, adherent glycocalyx material. Without limitation thereto, such organisms would include the ruminal cellulolytic bacteria such as *Ruminococcus albus, R. flavefaciens* and the like. Specific stains of *Ruminococcus* preferred for making the products of the invention include *R. albus*, strain 7, and *R. flavefaciens*, strains B34b and FD-1. Also of interest are *Clostridium* species, especially *C. thermocellum*. Two such strains that have indicated ability to produce glycocalyx material are ATCC 27405 and JW20. Also contemplated for use herein are cultures having all the identifying characteristics of the aforementioned strains.

Typically, the biomass fermentation with a ruminal cellulolytic bacterium will be conducted under anaerobic conditions on any suitable medium, such as a modified Dehority medium (MDM), described further in Example 1, below. Though it is possible to hasten the attainment of anaerobic conditions in the fermentation vessel prior to inoculation, such as by exposing the medium to strong light following addition of a chemical reducing agent, an anaerobic state is eventually reached during the fermentation. The fermentation would be conducted at a temperature within the range of about 35-42° C., preferably about 37-40° C. Typically, the cultivation will be conducted at a pH within the range of about 6.0-7.1, and preferably at a pH of 6.5-6.6. However, pH control is usually unnecessary. Occasional stirring or agitation of the culture will tend to facilitate complete colonization of the substrate by the cells, and thus production of the adhesins. The fermentation would typically be continued until the level of glycocalyx material production is optimized. With a 2% inoculum by volume, fermentation would be complete by 48 hours. At a lower inoculum rate (~0.5% by volume) without stirring, it may be necessary to continue the fermentation for a period of 3 to 5 days. *Clostridium* species are cultivated under similar anaerobic conditions, though a suitable fermentation temperature is in the range of about 57-62° C., and optimally about 60° C.

Isolation of the fermentation residue is accomplished by separating the rather sticky sediment layer (containing glycocalyx, embedded cells, and residual substrate) from the liquid phase. The separation can be effected by any means known in the art, to include decanting, siphoning, screening, filtering, centrifugation and the like in order to remove the preponderance of the medium, undigested substrate and residual cells and to recover the residue containing the glycocalyx material. The recovered residue may optionally be washed and dried, such as on a belt drier to a free-flowing particulate material (e.g. to a moisture level of 15-20% by weight). Further purification of the recovered residue is optional, depending on the prospective end use application. It is desirable to obtain the highest surface:mass ratio in the glycocalyx material, at least to the point of practicality. To this end, it may be desired to further grind the particles recovered from the drying operation, such as in a Wiley mill, and then to screen the material to eliminate oversized particles. With most biomass materials as the starting substrate, it is expected that recovered product having a maximum particle size on the order of 0.5 mm would strike an optimum balance between the economics of production and adhesive performance. For many specialized applications, it may be desirable to employ an even smaller particle size, such as a maximum screen size of 0.1 mm, 0.05 mm, or even 0.01 mm. When in the dry state, the recovered glycocalyx-containing material is a free-flowing powder. When plasticized by water or similar solvent, the material becomes sufficiently deformable for making a bond.

Recovered fermentation residues having relatively high (greater than about 30% (glycocalyx material) may be used, by itself, as an adhesive. At lower levels of glycocalyx material, the recovered fermentation residues described above more typically will be added a component to conventional adhesives, as a partial replacement therefore. Typical water-borne adhesives for use herein include urea-formaldehyde, melamine-formaldehyde, melamine-urea-formaldehyde, melamine-modified urea-formaldehyde, phenol-formaldehyde, resorcinol-formaldehyde, phenol-resorcinol-formaldehyde, phenol-urea-formaldehyde, furan-phenol-formaldehyde, furan-phenol-resorcinol-formaldehyde, poly (vinyl acetate), ethylene vinyl acetate polymers, poly (vinyl alcohol), water-borne epoxies, and emulsion polymerized isocyanate; adhesives derived from acrylics, starch, tannin, lignin, and lignosulfonate; and also adhesives derived from proteins, such as soybean, blood, casein, animal bone, and animal hide. Of particular interest is the use of the residues in adhesive formulations in combination with phenol-formaldehyde (PF).

The residues can be added to conventional adhesives in large amounts of at least 15%, 20%, 30%, 50%, or even 75% by weight (dry basis) without significant loss of the adhesive properties of the resin, itself. In the context of the amount of fermentation residue that is applied between two surfaces as an adhesive, an "effective amount" is defined herein as that amount which will produce a stable bond between those surfaces for whatever purpose those surfaces are being bonded together. Thus, for example, an effective amount of fermentation residue between veneer layers or exterior grade plywood would be that amount which will bind those layers together to withstand conditions according to established industry standards. In the context of an amount of fermentation residue that is used as partial replacement of a chemical adhesive, such as PF resin, an "effective amount" is defined herein as an amount that will yield a formulation comprising both the fermentation residue and the chemical adhesive, wherein the formulation will produce a stable bond between surfaces to which the formulation is applied. Adhesive formulations contemplated herein would also include extenders and other additives as known in the adhesive art.

The adhesives of the invention would be useful in bonding multiple layers or pieces of wood or other lignocellulosic material to one another, such as in the production of plywood, particleboard, pressboard, flakeboard, chipboard, veneered products, etc. In the production of plywood, the adhesive is applied to veneer surfaces by any of a variety of methods, such as spraying, roll coating, knife coating, or curtain coating. Two or more of the veneers are then laid-up to form sheets of required thickness. The mats or sheets are then placed in a heated press and compressed to effect consolidation and curing of the materials into a board. In the production of the aforementioned composite materials, wood materials such as flakes, fibers, particles, wafers, strips or strands are blended or sprayed with the adhesive material to form a uniform mixture. The materials are thereafter formed into a loose mat, which is compressed between heated platens in order to permanently bond the products together. Conventional processes are generally carried out at temperatures in the range of about 120-225° C. in the presence of steam generated by intrinsic moisture contained in the wood materials.

The following examples are intended to further illustrate the invention, without any intent for the invention to be limited to the specific embodiments described therein.

All references disclosed herein or relied upon in whole or in part in the description of the invention are incorporated by reference in their entirety.

Example 1

Preparation of *R. albus* Fermentation Residues Containing Bioadhesive from Microcrystalline Cellulose Preparation Procedure.

*Ruminococcus albus* (strain 7) and *Ruminococcus flavefaciens* (strains B34b and FD-1) were revived from 80° C. glycerol stocks, and were grown at 39° C. under a $CO_2$ atmosphere. The medium was a modified Dehority medium (MDM), which contained the following (per liter): 0.9 g $KH_2PO_4$, 3.2 g $Na_2CO_3$, 0.90 g NaCl, 0.73 g $NH_4Cl$, 0.085 g $MgCl_2.6H_2O$, 0.066 g $CaCl_2.2H_2O$, 0.028 g $MnCl_2.4H_2O$, 0.02 g $FeSO_4.7H_2O$, 0.01 g $ZnCl_2$, 0.002 g $CoCl_2.6H_2O$, 0.002 g resazurin, 0.5 g yeast extract, 1.0 g cysteine HCl, 10 ml of Schaefer's vitamin mixture (Schaefer et al., J. Dairy Sci. 63:1248-1263, 1980, but amended with 0.125 mg of tetrahydrofolic acid per liter of vitamin mix) and 0.067 ml each of isobutyric, 2-methylbutyric, n-valeric and isovaleric acids. For *R. albus* 7, the medium was also amended with 25 µM of 3-phenylpropanoic acid (PPA, Morrison et al., Appl. Environ. Microbiol. 56:3220-3222, 1990). Additional $Na_2CO_3$ was added from a saturated solution to adjust the initial pH of the medium to 6.9. The medium contained 4 g Sigmacell 50 microcrystalline cellulose (SC50) as the sole fermentable carbohydrate.

Fermentations to produce the residues for adhesive testing were carried out in 45 l glass carboys containing 40 l of the above medium, wherein the cellulose was either SC50 (3 g/l) or long fibrous cellulose CF1 (Sigma, 4 g/l) (Table 1). The medium (without cellulose) was filter-sterilized into carboys that contained the cellulose and enough water to hydrate the solids. The carboys had been previously sterilized by autoclaving (121° C., 60 min). Carboys were warmed to 39° C., gassed with $CO_2$ and illuminated with a bright incandescent light (Fukushima et al., Anaerobe 8:29-34, 2002) until the medium was fully anaerobic. (as revealed by decolorization of the resazurin). Carboys were then inoculated with 200 ml of late exponential-phase, cellulose-grown culture, and were vigorously swirled once or twice daily to suspend the cellulose particles and facilitate their complete colonization by the cells. After 88 to 108 h of incubation, the liquid phase was removed by siphoning, and the rather sticky sediment layer (containing glycocalyx, embedded cells, and residual cellulose) was resuspended in a small volume of deionized water. The resuspended material was centrifuged at 15,000×g for 45 min, and the supernatant discarded. Centrifugation always resulted in a small amount (<5% by volume) of a grey-colored layer of cells that sedimented atop the yellow glycocalyx; this layer was removed by careful scraping with a stainless steel spatula. The pellet, which contained primarily residual cellulose along with variable amounts of glycocalyx material and adherent cells, was lyophilized; these materials are designated LFR (lyophilized fermentation residue). In one case, a portion of the pellet was incorporated into the adhesive formulation while still wet, for comparison to the lyophilized material; this material was designated WFR (wet fermentation residue)

Composition of Fermentation Residues.

Lyophilized fermentation residues were analyzed for protein and for alkali-soluble carbohydrate after treating ~10 mg (weighed to 0.001 mg) of residue with 0.50 ml of 1 N NaOH at 70° C. for 1 h. Treated samples were neutralized by addition of 0.50 ml of 1 N HCl, and were centrifuged (12,000×g, 5 min). The supernatants were assayed for protein by the method of Bradford M M (Anal. Biochem. 72:248-254, 1976), using Coomassie Plus reagent (BioRad, Hercules, Calif.) with lysozyme as protein standard, and were assayed for alkali-soluble carbohydrate by the phenol-sulfuric acid method (Dubois et al., Anal. Chem. 28:350-356, 1956) with glucose as standard.

To remove cellular material for subsequent characterization of the glycocalyx, residues (1 g) were autoclaved (121° C., 45 min) in 100 ml of neutral detergent solution (Goering and Van Soest, Agricultural Handbook No. 379, Agricultural Research Service, United States Department of Agriculture, Washington, D.C., 1970). The solid residue was filtered onto 47 mm-diameter polycarbonate membranes (3 μm pore diameter; Poretics, Livermore, Calif.) and rinsed exhaustively with hot deionized water prior to lyophilization. Subsamples (10 mg) of the lyophilized neutral detergent fiber (NDF) were treated with 1 ml of 2 N trifluoroacetic acid at 120° C. for 1.5 h, dried under an air stream, resuspended in 1 ml of deionized water, and passed through Supelclean SAX anion exchange columns (Supelco, Bellefone, Pa.). Neutral sugars were determined by ion chromatography (Hatfield and Weimer, J. Sci. Food Agric. 69:185-196, 1995). The results of protein and carbohydrate analyses are reported in Table 2.

Example 2

Adhesive Preparation

R. albus Fermentation Residue from Microcrystalline Cellulose

The following adhesive sources were used for the construction of plywood panels: phenol formaldehyde (PF, 42% solids; Neste Resins Corp., Springfield, Oreg.); wet fermentation residue (WFR) from R. albus 7 fermentation as prepared in Example 1 (33% solids in water, never dried); and lyophilized fermentation residue (LFR) from four separate Ruminococcus fermentations as prepared in Example 1 (each mixed with water to 33% solids). The adhesives were formulated according to Table 3. When mixing the LPR and PF together, the LFR was initially mixed with water until smooth, and then the PF was added and mixed well. PF, when used without fermentation residue, was supplemented with GLU-X (The Robertson Corporation, Brownstown, Ind.), a wheat-derived protein and starch product commonly used as a glue extender.

Example 3

Plywood Panel Layup

R. albus Fermentation Residue from Microcrystalline Cellulose

Aspen veneer, 178×178×3 mm (7×7×⅛ inch) thick was conditioned to equilibrium moisture content at 27° C., 30% relative humidity (RH). Adhesive prepared as described in Example 2 was weighed onto veneers as required for the construction of three-ply panels and spread evenly across the veneer with a spatula. Veneer sheets were arranged in a cross-ply pattern (i.e., the wood grain in the middle sheet was oriented perpendicular to the grain of the outer sheets) and were pressed at 180° C. and 1.125 MPa (163 lb/in$^2$). The adhesives used, singly or in combination, along with pressing times, are shown in Table 3.

Example 4

Analysis of Adhesive Properties of Plywood Panels

R. albus Fermentation Residue from Microcrystalline Cellulose

Each three-ply panel as prepared in Example 3 was conditioned at 27° C., 30% RH for ~1 to 2 weeks before cutting into twelve standard lap shear specimens as outlined in PS 1-95 (National Institute of Science and Technology 1995). Six specimens from each panel were tested for dry shear strength using a universal testing machine at a loading rate of 1 cm/min. The remaining six specimens from each panel were subjected to a standard VPS treatment (National Institute of Standards and Technology 1995, Washington, D.C.). A vacuum of 85 kPa (25 in. of Hg) was drawn on the specimens while in water and held for 30 min. The vacuum was broken and a pressure of 450 to 480 kPa (65-70 lb in$^{-2}$) was applied to the specimens while still in water, and held for 30 min. Shear strength was determined on the wet specimens using a universal testing machine at a loading rate of 1 cm min$^{-1}$. Wood failure percentages were determined on the dry shear samples after testing and on wet shear specimens after testing and subsequent air drying using ASTM procedure D-5266-99 (American Society for Testing and Materials 1999, West Conshohocken, Pa.).

Figure 1B:
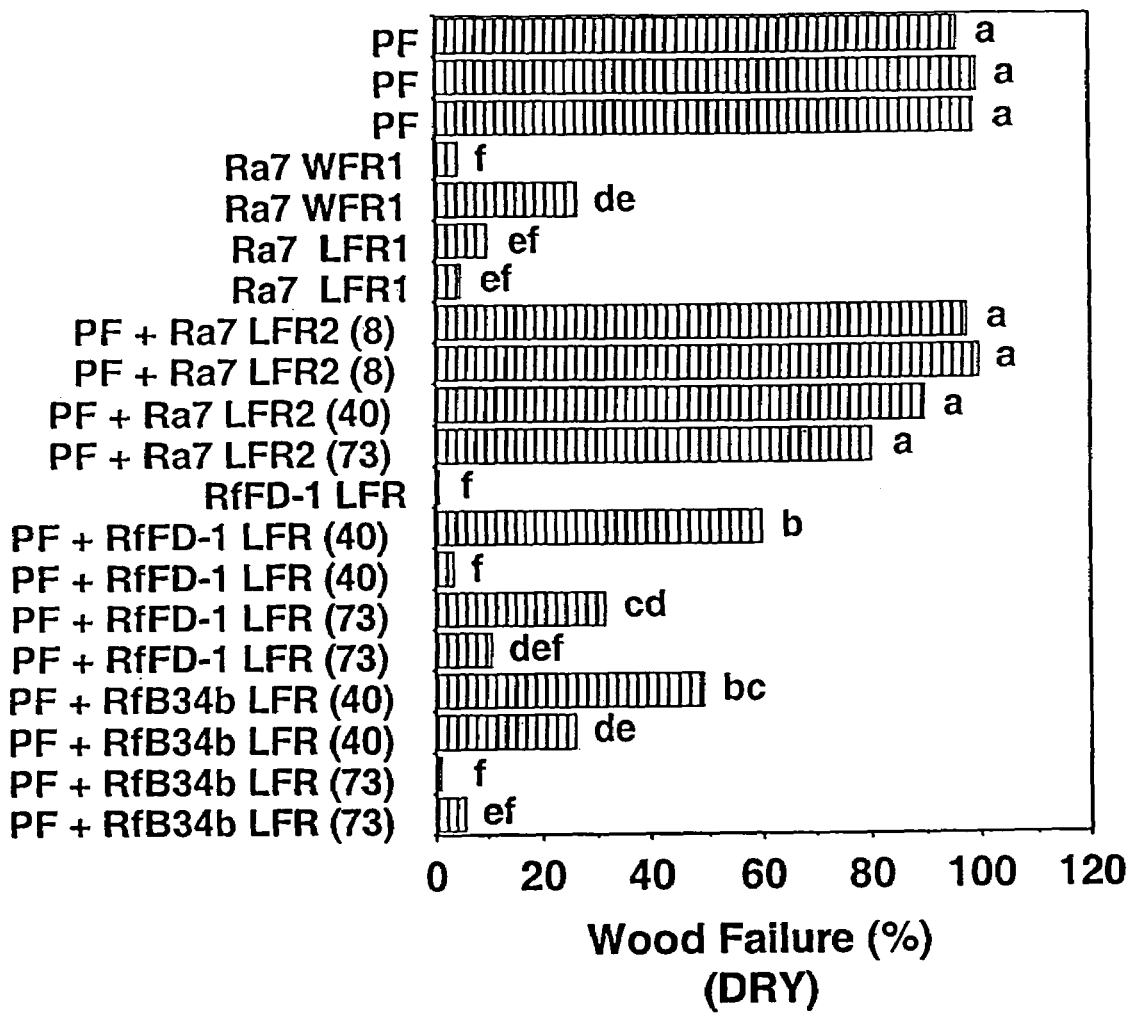
FIG. 1B is a bar graph illustrating wood failure percentage, for 3-ply aspen plywood panels prepared with adhesives (based on fermentation residue of microcrystalline cellulose) described in Table 3, tested under dry conditions. Numbers in parentheses indicate percentage of fermentation residue by weight in the adhesive formulation. Samples having different lower-case letters within treatments differ ($P<0.05$). Pooled standard error for shear strength=0.58 MPa. Pooled standard error for wood failure=16.9%.

The shear strength for panels tested under dry conditions are illustrated in FIG. 1A. The wood failure results for panels tested under dry conditions are illustrated in FIG. 1B.

Figure 2A:
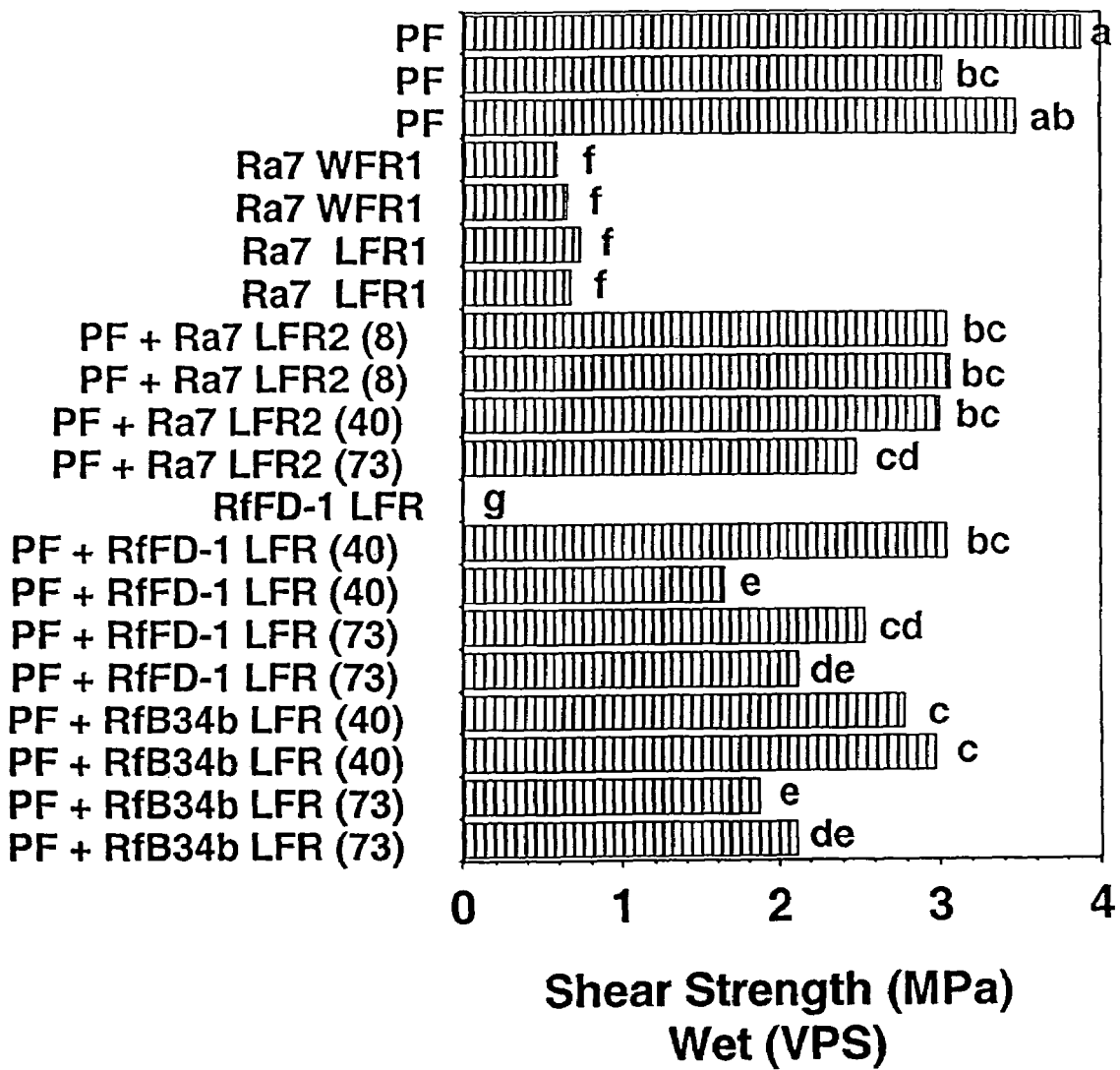
FIG. 2A is a bar graph illustrating shear strength.
Figure 2B:
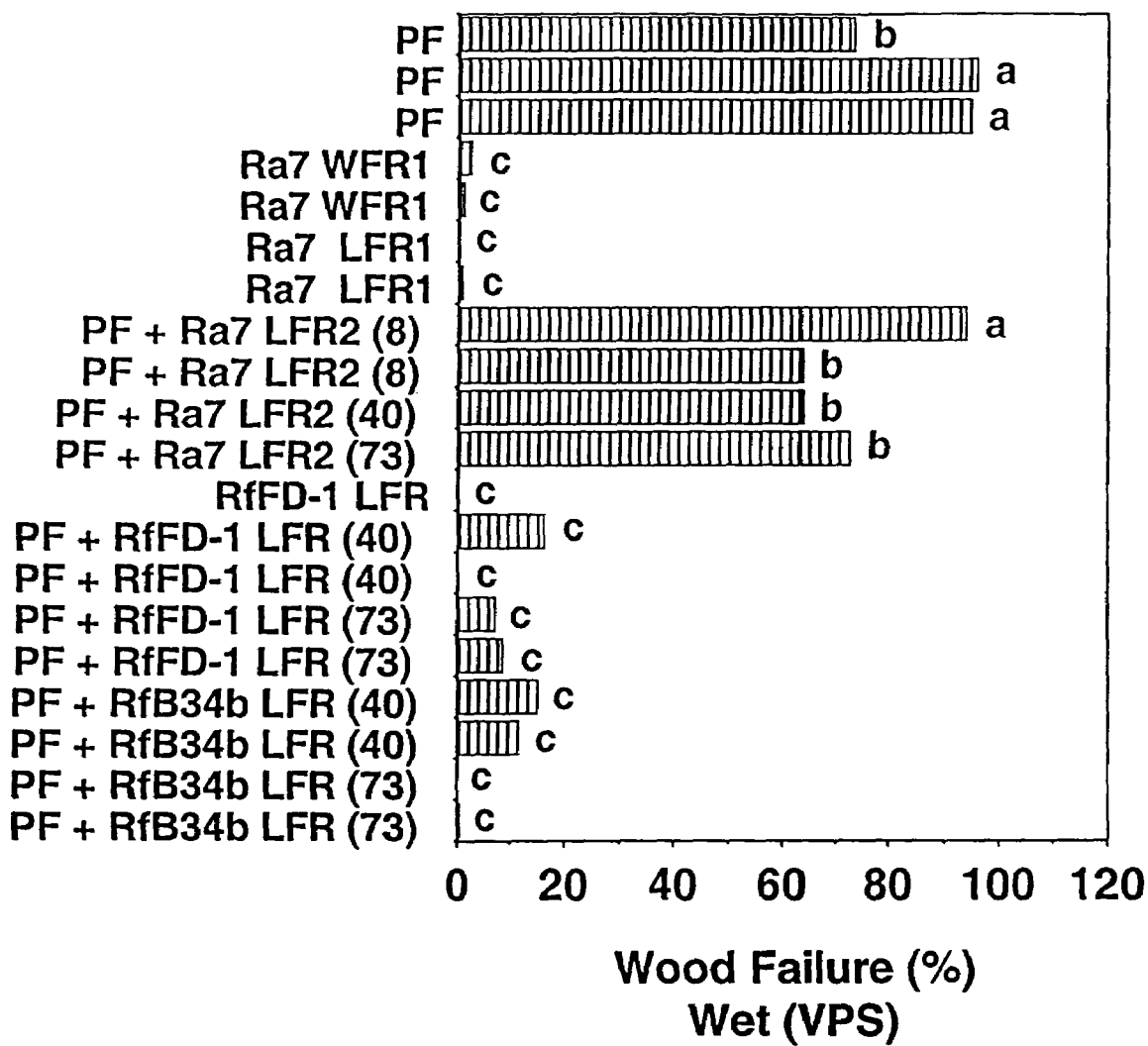
FIG. 2B is a bar graph illustrating wood failure percentage, for 3-ply aspen panels prepared with different adhesives (based on fermentation residue of microcrystalline cellulose), tested after vacuum/pressure/soak [VPS] treatment. Numbers in parentheses indicate percentage of fermentation residue by weight in the adhesive formulation. Samples having different lower-case letters within treatments differ ($P<0.05$). Pooled standard error for shear strength=0.46 MPa. Pooled standard error for wood failure=16.4%.

The shear strengths for panels tested after VPS treatment are illustrated in FIG. 2A. The wood failure results for panels tested after VPS treatment are illustrated in FIG. 2B.

Example 5

Preparation of *R. albus* Fermentation Residues Containing Bioadhesive from Alfalfa Fiber Alfalfa fiber from a wet fractionation process was air-dried and prepared inside a heated (39° C.) room. Fifty grams of air-dried alfalfa fiber was placed inside a custom-made column bioreactor consisting of a vertically-oriented, 29.4 cm×7 cm polycarbonate tube. Each end of the tube was capped with a tightly-sealed fitting for connection to rubber tubing. The interior face of the fitting included a fine-screened (30 micrometer) nylon mesh screen to contain the alfalfa particles. The bed of alfalfa was held against the bottom fitting by a stainless steel weight having a central hole of about 3 mm diameter to permit passage of liquid and gas; a stainless steel mesh screen was placed between the alfalfa fiber and the weight to contain particles. The entire unit was autoclaved for 15 min at 15 lb/in$^2$, after which Modified Dehority medium (MDM, 1.2 liters) was pumped into the reactor through a sterile filter, using a peristaltic pump. The reactor was gassed with a gentle stream of $CO_2$ during the pumping. The column reactor was inoculated through a separate port with 10 mL of a culture of *Ruminococcus albus* 7 (previously grown on MDM cellulose for 36-48 h). Culture medium was recirculated through the column reactor at a flow rate of approximately 2 mL per min. After 5 to 7 days, the residual solids (fermentation residue) in the column were removed (though the fermentation typically stabilized within 3 or 4 days), squeezed through paper towels reinforced with nylon thread, and freeze-dried.

Nine separate column reactor runs were made as described above. The average recovery of residue per run was 29.1 g. All of the residues were freeze-dried (except a small amount retained for compositional analysis) and were composited into a single batch for adhesives testing, either alone or in combination with phenol-formaldehyde residue.

Example 6

Large Scale Preparation of *R. albus* and *C. thermocellum* Fermentation Residues Containing Bioadhesive from Alfalfa Preparation Procedure.

Cultures of *R. albus* 7 and *C. thermocellum* ATCC 27405 were revived from glycerol stocks at −80° C. and were grown as pure cultures in anaerobic test tubes under a $CO_2$ atmosphere in modified Dehority medium containing Sigmacell 50 microcrystalline cellulose as sole fermentable carbohydrate (see Example 1). The incubation temperatures for *R. albus* and *C. thermocellum* were 39° C. and 60° C., respectively. Cultures of both organisms were scaled to 4-10 L in glass carboys containing the same medium, but with ground alfalfa fiber replacing cellulose as substrate. The carboys were used to inoculate modified 380 L fermentors (Fermentation Design, working volume 300 L, inoculum volume ~11 L). These fermentations were carried out for 50 h.

For both cultures, the fermentation residues were recovered by pumping the fermentor contents through a 30.5 cm (12-inch) Sperry plate-and-frame filter press fitted with 14 cellulose filter sheets (32 cm×32 cm×0.16 mm, grade 901 paper, BIF America). The filters were hand-scraped to remove the fermentation residue (containing residual fiber, glycocalyx and adherent bacterial cells), which was then freeze-dried. The lyophilized fermentation residue (LFR) was ground through a Wiley mill (0.5 mm screen) and used directly for adhesive formulations.

Example 7

Adhesive Preparation

*R. albus* and *C. thermocellum* Fermentation Residues Containing Bioadhesive from Alfalfa The following adhesive sources, shown in Table 4, were used for the construction of plywood panels:

5778ext: phenol-formaldehyde plywood resin (Georgia-Pacific Resins, Inc., Decatur, Ga.) having 42% solids with added walnut shell flour and GLU-X (The Robertson Corporation, Brownstown, Ind.) at a combined level of 30% of total solids;

unalf30%: gp5778 resin with unfermented alfalfa added (30% of total solids);

alfRA30%: gp5778 resin with Ra7 lyophilized fermentation residue (LFR) of alfalfa added (30% total solids);

alfRA45%: gp5778 resin with ground Ra7 LFR from Example 6 added (45% total solids);

alfCT30%: gp5778 resin with ground Ra7 LFR from Example 6 added (30% total solids);

alfCT45%: gp5778 resin with ground Ra7 LFR from Example 6 added (45% total solids).

When mixing the LFR and resin together, the LFR was initially mixed with water until smooth, and then the resin was added and mixed well.

Example 8

Plywood Panel Layup

*R. albus* and *C. thermocellum* Fermentation Residues Containing Bioadhesive from Alfalfa Aspen veneer, 178×178×3 mm (7×7×⅛ inch) thick was conditioned to equilibrium moisture content at 27° C., 30% relative humidity (RH). Adhesive prepared as described in Example 7 was weighed onto veneers at the rate of 7 g/glueline as required for the construction of three-ply panels and spread evenly across the veneer with a spatula. Veneer sheets were arranged in a cross-ply pattern (i.e., the wood grain in the middle sheet was oriented perpendicular to the grain of the outer sheets) and were pressed at 180° C. and 1.14 MPa (0.165 lb/in$^2$) for 5 min. The three-ply test panels were conditioned at 27° C. and 26% RH for 1 week. Thereafter, the panels were cut into lap-shear specimens, 82.5×25.4 mm. (3¼×1 in) and evaluated for wet and dry shear strength and wet and dry wood failure by procedures described in Example 4.

Figure 3A:
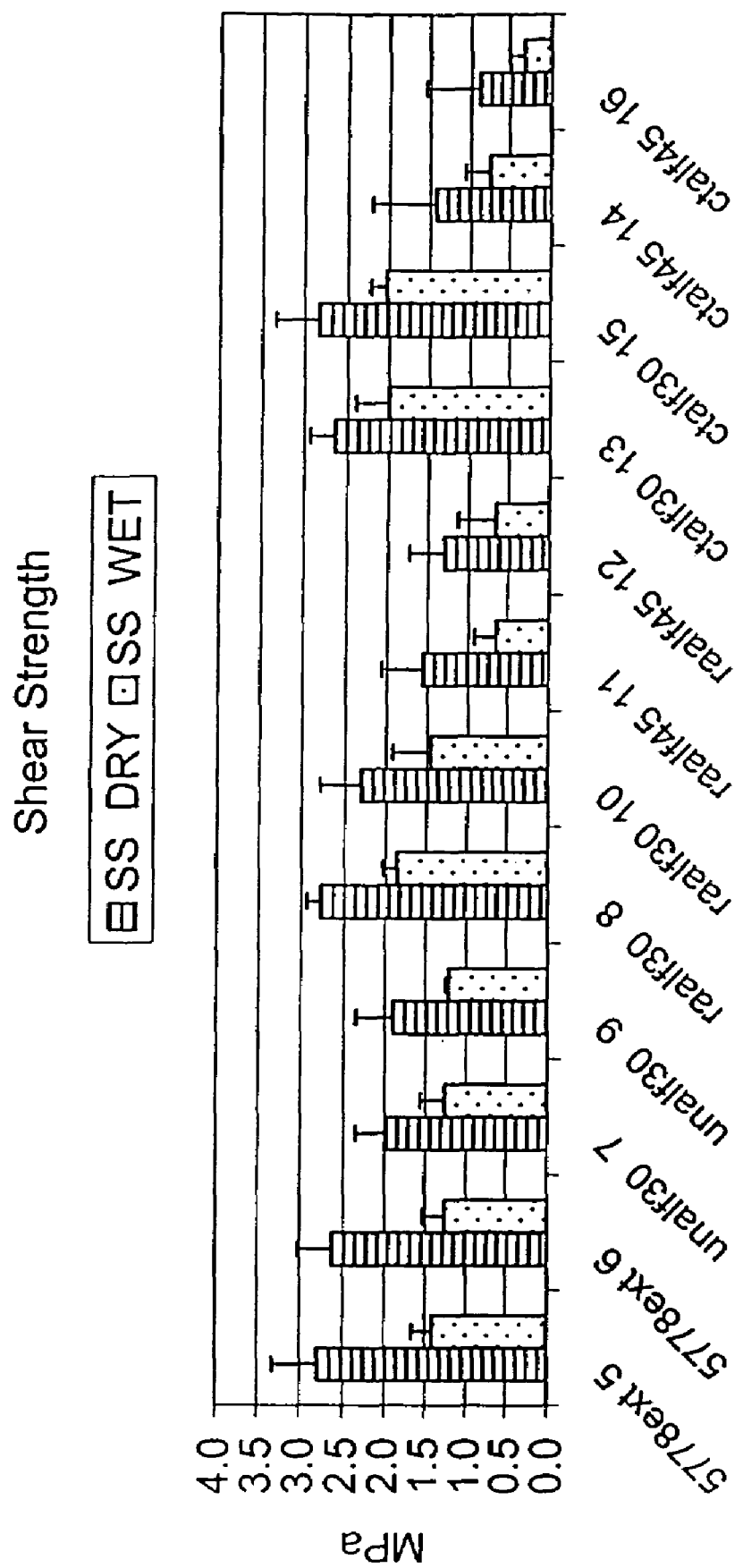
FIG. 3A is a bar graph comparing shear strength for 3-ply aspen plywood panels prepared with adhesives (based on fermentation residue of alfalfa fiber) tested under dry conditions with shear strength for similarly made panels after VPS treatment. 5778ext=phenol-formaldehyde plywood resin having 42% solids with added walnut shell flour and GLU-X in equal amounts by weight at a combined level of 30% of total solids; unalf30=gp5778 resin with unfermented alfalfa added (30% of total solids); raalf30=gp5778 resin with Ra7 lyophilized fermentation residue (LFR) of alfalfa added (30% total solids); raalf45=gp5778 resin with ground Ra7 LFR from Example 6 added (45% total solids); ctalf30=gp5778 resin with ground Ra7 LFR from Example 6 added (30% total solids); ctalf45 gp5778 resin with ground Ra7 LFR from Example 6 added (45% total solids).
Figure 3B:
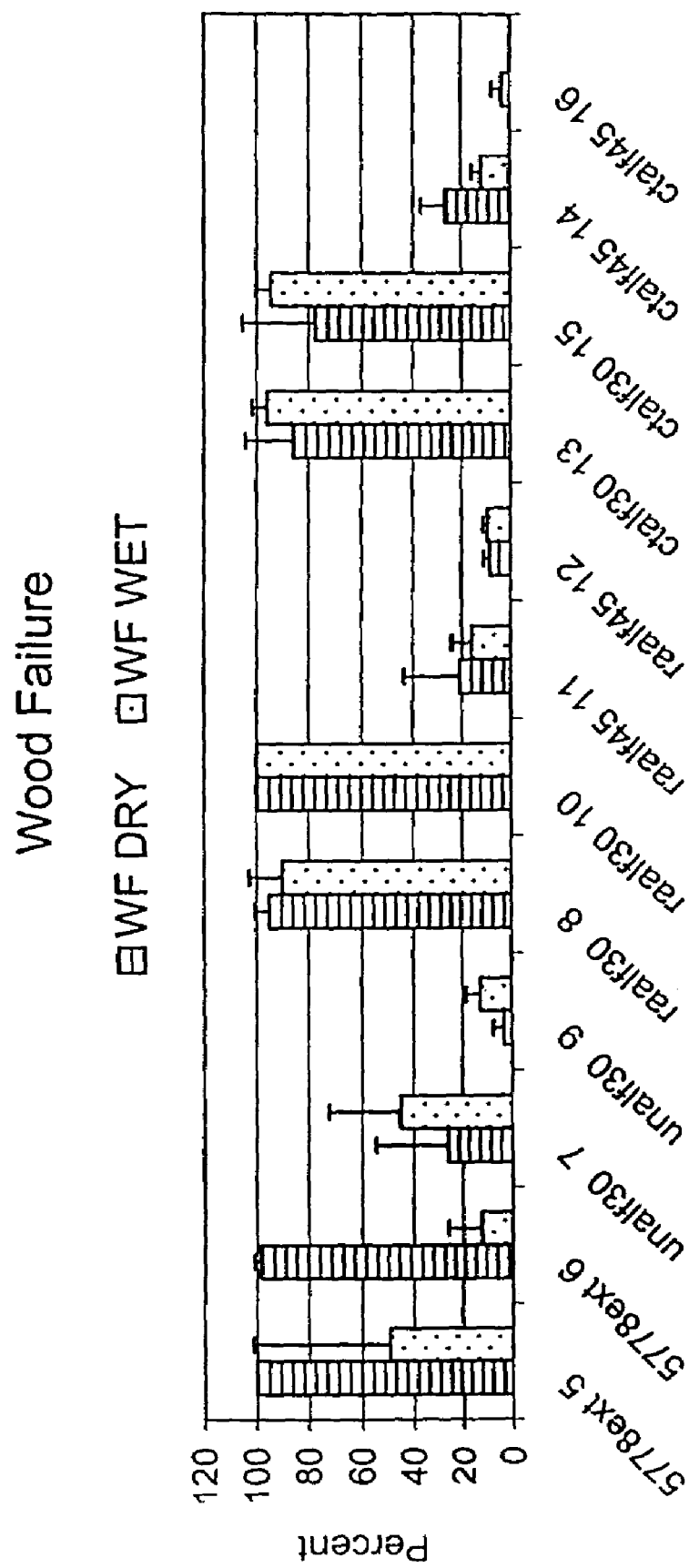
FIG. 3B is a bar graph comparing wood failure for 3-ply aspen plywood panels prepared with adhesives (based on fermentation residue of alfalfa fiber) tested under dry conditions with wood failure for similarly made panels after VPS treatment. Legends are the same as for FIG. 3A.

The shear strength for panels tested under dry conditions and after VPS treatment are illustrated in FIG. 3A. The wood failure results for panels tested under dry conditions and after VPS treatment are illustrated in FIG. 3B.

Example 9

Bonding Properties of Glycocalyx Material without Phenol-Formaldehyde Resin To test bonding of glycocalyx material without phenol-formaldehyde, small 50.8×50.8 mm (2×2×⅜ in) specimens were made of coarse ground alfalfa, unfermented and fermented with R. albus 7. Seventeen grams of dry alfalfa plus 17 g water were mixed well and formed into a mat, then pressed to 9.5 mm (⅜ in) thick at 180° C. for 5 min. The Ra7 fermented alfalfa specimen bonded together, but the unfermented alfalfa was not bonded in the center of the specimen and became two pieces when it was removed from press.

Statistics.

Analysis of variance in each of the above examples was performed using the ANOVA protocol of the SAS system (SAS Institute, Cary, N.C., 1998). Mean separations were performed using Duncan's multiple range test, at a significance level of $P<0.05$.

TABLE 1

Growth conditions for generating fermentation residues

| Residue[a] | Bacterium | Cellulose source and amount (g) | Incubation time (h) | Residue dry weight (g) |
|---|---|---|---|---|
| Ra7 WFR1 | R. albus 7 | CF1 (160) | 88 | NT[b] |
| Ra7 LFR 2 | R. albus 7 | SC50 (120) | 108 | 25.6 |
| RfB34b LFR | R. flavefaciens FD-1 | SC50 (120) | 100 | 79.5 |
| RfFD-1 LFR | R. flavefaciens B34b | SC50 (120) | 96 | 80.2 |

[a]FR, fermentation residue that was tested either wet (WFR) or lyophilized and rehydrated (LFR).
[b]NT, not tested

TABLE 2

Composition of fermentation residues

| | Protein | Alkali-soluble CHO | Mol % neutral sugar composition of TFA hydrolyzate of NDF[b] | | | | |
|---|---|---|---|---|---|---|---|
| | (% dry wt) | (% dry wt)[a] | Glc | Gal | Man | Xyl | Ara |
| Ra7 FR1 | 4.88 ± 0.14 | 23.1 ± 2.1 | | | NT[c] | | |
| Ra7 LFR 2 | 3.77 ± 0.13 | 20.3 ± 0.1 | 69.2 ± 0.6 | 2.3 ± 0.3 | 8.3 ± 0.3 | 19.4 ± 0.5 | 0.5 ± 0.2 |
| RfB34b LFR | 0.42 ± 0.01 | 13.6 ± 1.1 | 72.2 ± 1.9 | 1.9 ± 0.1 | 7.4 ± 0.5 | 18.0 ± 1.3 | 0.2 ± 0.1 |
| RfFD-1 LFR | 1.41 ± 0.01 | 22.4 ± 6.9 | 73.1 ± 0.4 | 2.6 ± 0.5 | 7.3 ± 0.3 | 16.8 ± 0.5 | 0.3 ± 0.1 |
| Ctc 27405 LFR | NT[c] | NT[c] | 61.0 ± 9.4 | 4.8 ± 3.4 | 13.1 ± 3.0 | 21.3 ± 2.9 | <0.1 |

[a]Percentage of residue dry matter converted to phenol/sulfuric acid-reactive carbohydrate after treatment with 1 N NaOH, 70° C., 1 h. Results are mean values of duplicate samples ± S.E.M.
[b]Neutral detergent fiber of residue isolated by the method of Goering and Van Soest (1970). See text for details of TFA hydrolysis. Results are mean values of duplicates samples ± S.E.M. Rhamnose and fucose were <0.2% for all samples.
[c]NT = Not tested

TABLE 3

Adhesive formulations and pressing times used to produce aspen plywood sheets

| Adhesive[a] | PF (g)[c] | GLU-X (g)[c] | FR[b] (g)[c] | H₂O (g) | Press time (min) | Number of panels |
|---|---|---|---|---|---|---|
| PF | 18.9 | 3.9 | 0 | 0 | 5 | 3 |
| Ra7 WFR1 | 0 | 0 | 9.24 | 0 | 10 | 2 |
| Ra7 LFR 1 | 0 | 0 | 11 | 22 | 10 | 2 |
| PF + Ra7 LFR 2 (8) | 11.76 | 0 | 2 | 0 | 10 | 2 |
| PF + Ra7 LFR 2 (40) | 2.94 | 0 | 2 | 4 | 5 | 1 |
| PF + Ra7 LFR 2 (73) | 1.47 | 0 | 4 | 8 | 8 | 1 |
| RfB34b LFR | 0 | 0 | 11 | 22 | 10 | 2 |
| RfFD-1 LFR | 0 | 0 | 11 | 22 | 10 | 2 |
| PF + RfB34b LFR (40) | 2.94 | 0 | 2 | 4 | 10 | 2 |
| PF + RfB34b LFR (73) | 1.47 | 0 | 4 | 8 | 10 | 2 |
| PF + RfFD-1 LFR (40) | 2.94 | 0 | 2 | 4 | 10 | 2 |
| PF + RfFD-1 LFR (73) | 1.47 | 0 | 4 | 8 | 10 | 2 |

[a]LFR = lyophilized fermentation residue, WFR = wet fermentation residue. Ra7, Ruminococcus albus 7; RfB34b, R. flavefaciens B34b; RfFD-1, R. flavefaciens FD-1. Values in parentheses correspond to percentage by weight of fermentation residue.
[b]Fermentation residue (WFR or LFR)
[c]Dry weight basis

TABLE 4

Adhesive formulations and pressing times used to produce aspen 3-ply panels

| Adhesive[a] | PF (g) | Glu-x + walnut shell flour (1:1) (g) | AR[b] (g) | H₂O (g) |
|---|---|---|---|---|
| 5778ext | 69.0 | 12.7 | 0 | 18.3 |
| unalf30 | 69.0 | 0 | 12.7 | 18.3 |
| raalf30 | 69.0 | 0 | 12.7 | 18.3 |
| ctalf30 | 69.0 | 0 | 12.7 | 18.3 |
| raalf45 | 37.0 | 0 | 12.7 | 50.3 |
| ctalf45 | 37.0 | 0 | 12.7 | 50.3 |

[a]The phenol formaldehyde resin, PF (GP5778) contains 42% solids. 30 = 30% of total solids, 45 = 45% of total solids.
[b]Alfalfa residue (alf), unfermented (un) or fermented (ra or ct).

We claim:

1. A method for binding together surfaces brought into an adjacent relationship with one another, comprising applying to at least one of said surfaces an adhesive composition comprising a glycocalyx-containing fermentation residue.

2. A method as described in claim 1, wherein said adhesive composition further comprises a conventional adhesive component.

3. A method as described in claim 2, wherein said conventional adhesive component is phenol-formaldehyde.

4. A method as described in claim 1, wherein the fermentation residue is the product of fermenting a cellulosic substrate with a glycocalyx-producing microorganism.

5. A method as described in claim 4, wherein the microorganism is a bacterium selected from the group consisting of *Ruminococcus* species and *Clostridium* species.

6. A method as described in claim 4, wherein the microorganism is selected from the group consisting of *Ruminococcus albus Ruminococcus flavefaciens*, and *Clostridium thermocellum*.

7. A method as described in claim 4, wherein the microorganism is a bacterium having all the identifying characteristics of a microorganism selected from the group consisting of *Ruminococcus albus* NRRL B-30653, *Ruminococcus flavefaciens* NRRL B-30654, *Ruminococcus flavefaciens* strain B34b, and *Clostridium thermocellum* ATCC 27405.

8. A method as described in claim 1, wherein the amount of said glycocalyx-containing fermentation residue is at least about 15% by weight of the composition.

9. A method as described in claim 1, wherein said surfaces are surfaces of a wood material.

* * * * *